United States Patent [19]

Blank et al.

[11] 4,348,336

[45] Sep. 7, 1982

[54] PROCESS FOR THE ISOLATION OF 1-NAPHTHYLAMINE-4,6- AND 1-NAPHTHYLAMINE-4,7-DISULPHONIC ACID

[75] Inventors: Heinz U. Blank, Odenthal; Horst Behre, Odenthal-Eikamp; Hans W. Linden, Leverkusen, all of Fed. Rep. of Germany

[73] Assignee: Bayer Aktiengesellschaft, Leverkusen, Fed. Rep. of Germany

[21] Appl. No.: 247,414

[22] Filed: Mar. 25, 1981

[30] Foreign Application Priority Data

Apr. 5, 1980 [DE] Fed. Rep. of Germany ....... 3013276

[51] Int. Cl.$^3$ ............................................. C07C 143/60
[52] U.S. Cl. .................................................... 260/508
[58] Field of Search ......................................... 260/508

[56] References Cited

U.S. PATENT DOCUMENTS 3,979,445  9/1976  Ross et al. ........................... 260/508
4,199,529  4/1980  Bonath et al. ....................... 260/508

Primary Examiner—Nicky Chan
Attorney, Agent, or Firm—Sprung, Horn, Kramer & Woods

[57] ABSTRACT

Process for the isolation of 1-naphthylamine-4,6- or 1-naphthylamine-4,7-disulphonic acid from sulphonation mixtures obtained in the sulphonation of 1-naphthylamine-6- or 1-naphthylamine-7-sulphonic acid with sulphuric acid and sulphur trioxide, wherein the aqueous solutions or suspensions formed, when the sulphonation mixtures are introduced into water, are warmed to 80° to 120° C., optionally kept for a period of time at this temperature, are then cooled to temperatures below 70° C., and the 1-naphthylamine-4,6- or 1-naphthylamine-4,7-disulphonic acid which has crystallized out is finally filtered off.

4 Claims, No Drawings

PROCESS FOR THE ISOLATION OF 1-NAPHTHYLAMINE-4,6- AND 1-NAPHTHYLAMINE-4,7-DISULPHONIC ACID

The invention relates to a process for the isolation of 1-naphthylamine-4,6- and 1-naphthylamine-4,7-disulphonic acid from the reaction mixture obtained in the sulphonation of 1-naphthylamine-6- or 1-naphthylamine-7-sulphonic acid.

1-Naphthylamine-4,6- and 1-naphthylamine-4,7-disulphonic acid are important intermediate products for the preparation of dyestuffs. They are prepared industrially by sulphonation of 1-naphthylamine-6- or 1-naphthylamine-7-sulphonic acid (see Ullmanns Enzyklopädie der technischen Chemie (Ullmanns Encyclopaedia of Industrial Chemistry), 4th edition, Volume 17, page 112 (1979)). It is necessary to isolate the two disulphonic acids from the sulphonation mixtures in order to remove undesired by-products. 1-Naphthylamine-4,6- and 1-naphthylamine-4,7-disulphonic acid are usually isolated as acid alkali metal salts. This isolation is effected by introducing the particular sulphonation mixtures into water, salting out the products by means of sodium chloride (see N. Donaldson "The Chemistry and Technology of Naphthalene Compounds" 1958, page 203) or sodium sulphate (see Czechoslovak Patent Specification No. 129,210), and filtering off and washing the salts which have crystallised out. 1-Naphthylamine-4,6-disulphonic acid can also be separated off as the sparingly soluble magnesium salt (see Czechoslovak Patent Specification No. 112,946).

This isolation of the acid alkali metal salts of the 1-naphthylamine-4,6- and -4,7-disulphonic acids is, however, associated with considerable difficulties, because the salts are obtained in the form of a fine crystal sludge, and frequently even as thixotropic masses, and can be only poorly filtered off and washed. In addition, the sulphonic acid salts filtered off contain troublesome amounts of salt, for example sodium chloride.

Another disadvantage of these known procedures is, furthermore, that large amounts of salt solution, for example sodium chloride solution, are necessary for the rinsing operation, and that the dilute acid obtained after filtering off the sulphonic acid salts contains considerable amounts of salts, which makes reprocessing of the dilute acid difficult.

It has now been found that the abovementioned disadvantages in the isolation of 1-naphthylamine-4,6- and -4,7-disulphonic acid can be avoided when the aqueous solutions or suspensions formed when the particular sulphonation mixtures are introduced into water are warmed or are allowed to warm to 80° to 120° C., preferably 90° to 115° C., and salting out is dispensed with, and instead, the free naphthylaminedisulphonic acids are separated out from the aqueous solutions or suspensions, warmed to 80° to 120° C., of the sulphonation mixtures by cooling.

In this procedure, the free 1-naphthylamine-4,6- and 1-naphthylamine-4,7-disulphonic acids crystallise out, in high yield and purity, in the form of crystalline precipitates which can easily be filtered off. Only a little dilute sulphuric acid is required for washing out the crystalline precipitates filtered off. The dilute acid obtained after filtering off the 1-naphthylamine-4,6- or 1-naphthylamine-4,7-disulphonic acid is free from salts and can therefore be worked up without difficulty.

The invention thus relates to a process for the isolation of 1-naphthylamine-4,6- and 1-naphthylamine-4,7-disulphonic acid from sulphonation mixtures obtained in the sulphonation of 1-naphthylamine-6- or 1-naphthylamine-7-sulphonic acid with sulphuric acid and sulphur trioxide; the process is characterised in that the aqueous solutions or suspensions formed when the sulphonation mixtures are introduced into water are warmed to 80° to 120° C., preferably 90° to 115° C., and the resulting solutions or suspensions of the sulphonation mixtures are cooled to temperatures below 70° C., preferably to temperatures from 20° to 60° C., optionally after they have been kept at the higher temperatures for a period, and the 1-naphthylamine-4,6- or 1-naphthylamine-4,7-disulphonic acid which has crystallised out is filtered off.

The heat of dilution released when the sulphonation mixtures are introduced into water is advantageously utilised for warming, according to the invention, the aqueous solutions or suspensions of the sulphonation mixtures to 90° to 120° C. That is to say, the sulphonation mixtures are advantageously added to the initially introduced water at a rate such that the temperature of the solutions or suspensions formed rises to 80° to 120° C. without additional warming or without cooling. If the sulphonation mixture is introduced more slowly, warming must take place if necessary, and if the rate of introduction chosen is higher, cooling must be effected if necessary.

For isolation of 1-naphthylamine-4,6-disulphonic acid, it has proved particularly suitable to warm the aqueous solutions or suspensions of the sulphonation mixtures to 90° to 110° C., and for the isolation of 1-naphthylamine-4,7-disulphonic acid, warming to temperatures of 100° to 115° C. has proved particularly suitable.

The amount of water which is to be initially introduced and to which the sulphonation mixture is added is advantageously chosen such that the sulphuric acid concentration in the dilute aqueous solution or suspension of the sulphonation mixtures is about 10 to 70% by weight, preferably 25 to 60% by weight. For the isolation of 1-naphthylamine-4,6-disulphonic acid, a sulphuric acid concentration of 40 to 60% by weight has proved particularly suitable, and for the isolation of 1-naphthylamine-4,7-disulphonic acid, a sulphuric acid concentration of 25 to 40% by weight has proved particularly suitable.

The 1-naphthylamine-disulphonic acids which have crystallised out are advantageously filtered off at temperatures from 20° to 60° C.

The process according to the invention is suitable for the isolation of 1-naphthylamine-4,6- and 1-naphthylamine-4,7-disulphonic acid from all sulphonation mixtures obtained in the sulphonation of 1-naphthylamine-6- and 1-naphthylamine-7-sulphonic acids with sulphuric acid and sulphur trioxide, independently of the reaction conditions used in the sulphonation.

The process according to the invention can be carried out, for example, as follows: the water required for diluting the sulphonation mixture is initially introduced into a stirred apparatus. The sulphonation mixture is then introduced, whilst stirring, at a rate such that the solution or suspension formed warms to a temperature from 80° to 120° C. and, if a suspension is formed, this remains easily stirrable at all times. If the desired temperature within the range of 90° to 120° C. has not already been achieved as a result of the heat of dilution, when the introduction has ended, the resulting aqueous solution or suspension is warmed to the desired temperature within the range indicated. In the case of 1-naphthylamine-4,7-disulphonic acid in particular, it has proved suitable subsequently to stir the resulting aqueous solution or suspension at 110° C., 100° C. and 90° C., in each case for one hour. The hot solution or suspension is then cooled slowly to temperatures below 70° C., preferably to 20° to 60° C., whilst stirring. The crystalline precipitate which has separated out is filtered off and washed with a little dilute sulphuric acid (for example 40 to 60% strength sulphuric acid).

The 1-naphthylamine-disulphonic acids obtained in this manner are distinguished by a high purity; their content of by-products lies below 2% by weight.

EXAMPLE 1

1,650 g of water are initially introduced into a stirred apparatus, and 1,171 g of the sulphonation mixture described below are added at a rate such that the suspension which forms remains easily stirrable. During the introduction, the temperature rises to 95° to 100° C. The aqueous suspension is then warmed to about 110° C., whilst stirring, is kept at this temperature for one hour and is then stirred at 100° C. and 90° C., in each case for one hour. It is then cooled slowly to 20° C., whilst stirring. The precipitate is filtered off and washed twice with a little 35% strength sulphuric acid.

460 g of 1-naphthylamine-4,7-disulphonic acid are obtained in the form of slightly grey crystals moistened with sulphuric acid.

The composition of the product was determined by high pressure liquid chromatography and thin layer chromatography. It is: 61.5% by weight of 1-naphthylamine-4,7-disulphonic acid; 0.05% by weight of 1-naphthylamine-7-sulphonic acid; 0.05% by weight of 1-naphthylamine-2,4,7-trisulphonic acid; and about 0.7% by weight of unknown impurities; the remainder to make up to 100% is sulphuric acid and water.

The sulphonation mixture used had been obtained as follows:

700 g of monohydrate were initially introduced into a 1 l stirred apparatus, and 225 g of 1-naphthylamine-7-sulphonic acid (about 99% pure) were added. 246 g of oleum (65% strength) were then added dropwise in the course of 30 minutes and the sulphonation mixture was stirred at 30° C. for about 8 hours.

EXAMPLE 2

The procedure followed is as described in Example 1, but instead of the 1,650 g of water, 1,550 g are initially introduced, and a sulphonation mixture which was obtained as described below is used.

505 g of 1-naphthylamine-4,7-disulphonic acid are obtained in the form of slightly grey crystals moistened with sulphuric acid.

The composition of the product was determined by high pressure liquid chromatography and thin layer chromatography. It is: 54.6% by weight of 1-naphthylamine-4,7-disulphonic acid; 0.05% by weight of 1-naphthylamine-7-sulphonic acid; 0.05% by weight of 1-naphthylamine-2,4,7-trisulphonic acid; and about 1.5% by weight of unknown impurities; the remainder to make up to 100% is sulphuric acid and water.

The sulphonation product used had been obtained as follows:

700 g of monohydrate were initially introduced into a 1 l stirred apparatus, and 225 g of 1-naphthylamine-7-sulphonic acid (about 99% pure) were added. 185 g of oleum (65% strength) were then added at 30° C. and the sulphonation mixture was stirred at 30° C. for about 24 hours.

EXAMPLE 3

1,920 g of water are initially introduced into a stirred apparatus, and 1,518 g of the sulphonation mixture described below are added, whilst stirring, at a rate such that the resulting suspension warms to 100° to 105° C. The suspension is then warmed to 110° C. and kept at 110° C., 100° C. and 90° C., in each case for one hour. The suspension is then cooled slowly to 60° C., kept at this temperature for one hour and then filtered at 60° C. The filter cake is washed with a little 40% strength sulphuric acid. 458 g of 1-naphthylamine-4,7-disulphonic acid are obtained in the form of slightly grey crystals moistened with sulphuric acid.

The composition of the product was determined by high pressure liquid chromatography and thin layer chromatography. It is: 50.6% by weight of 1-naphthylamine-4,7-disulphonic acid; 0.05% by weight of 1-naphthylamine-7-sulphonic acid; 0.05% by weight of 1-naphthylamine-2,4,7-trisulphonic acid; and about 1.5% by weight of unknown impurities; the remainder to make up to 100% is water and sulphuric acid.

The sulphonation mixture used had been obtained as follows:

713 g of monohydrate were initially introduced into a 1 l stirred apparatus, and 225 g of 1-naphthylamine-7-sulphonic acid (about 99% pure) were added. 580 g of oleum (65% strength) were then added at 30°–35° C. and the sulphonation mixture was stirred at 25° C. for about 14 hours.

EXAMPLE 4

1,434 g of water are initially introduced into a stirred apparatus, and 1,232.8 g of the sulphonation mixture described below are added in the course of 10 minutes. During this addition, the temperature rises to about 95° C.; after a short time, the 1-naphthylamine-4,6-disulphonic acid starts to crystallise out. The mixture is then allowed to cool to about 20° C. in the course of about 6 hours, whilst stirring slowly, and the crystalline precipitate is filtered off and washed twice with in each case 100 ml of 40% strength sulphuric acid. The filter cake is sucked thoroughly dry.

321 g of 1-naphthylamine-4,6-disulphonic acid are obtained in this manner in the form of slightly pink-coloured crystals moistened with sulphuric acid.

The composition of the product was determined by high pressure liquid chromatography and thin layer chromatography. It is: 76.1% by weight of 1-naphthylamine-4,6-disulphonic acid; 0.1% by weight of 1-naphthylamine-3,6-disulphonic acid; a trace of 1-naphthylamine-2,4,6-trisulphonic acid; and 23.7% by weight of sulphuric acid/water.

The sulphonation mixture used had been obtained as follows:

226.8 g of 1-naphthylamine-6-sulphonic acid (98.3%) were added to 760 g of initially introduced monohydrate in a 1 l stirred apparatus. 246 g of oleum (65% strength) were then added dropwise at 30° C. in the course of 30 minutes. The sulphonation mixture was then subsequently stirred at 30° C. for 16 hours.

EXAMPLES 5 to 7

The procedure followed was as described in Example 1, but instead of the 1,434 g of water, 962 g of water were initially introduced in Example 5, 647 g of water were initially introduced in Example 6 and 647 g of water were initially introduced in Example 7 and different sulphuric acid concentrations were in this manner established in the aqueous solutions or suspensions of the sulphonation mixtures. Furthermore, the 1-naphthylamine-4,6-disulphonic acid which had crystallised out was filtered off at 40° C. in Example 5, at 40° C. in Example 6 and at 60° C. in Example 7, and washed twice with in each case 100 ml of 50% strength sulphuric acid.

The composition of the 1-naphthylamine-4,6-disulphonic acid isolated under the various conditions is given in the following table.

TABLE

| Example No. | Amount of water initially introduced | % by weight of $H_2SO_4$ in the aqueous solution or suspension | Filtration temperature °C. | Yield of crystallised product g | Composition of the crystallised product (in % by weight) | | | |
|---|---|---|---|---|---|---|---|---|
| | | | | | -naphthylamine-4,6-disulphonic acid | 1-naphthylamine-3,6-disulphonic acid | 1-naphthylamine-2,4,6-trisulphonic acid | $H_2O/H_2SO$ |
| 5 | 962 | 50 | 40 | 311.7 | 80.0 | 0.2 | 0.1 | 19.7 |
| 6 | 647 | 60 | 40 | 327 | 73.3 | 0.4 | 0.2 | 26.1 |
| 7 | 647 | 60 | 60 | 310.4 | 77.5 | 0.4 | trace | 22.0 |

*The composition of the crystallised products was determined by means of high pressure liquid chromatography and thin layer chromatography.

EXAMPLE 8

1,090 g of water are initially introduced into a stirred apparatus, and 1,005 g of the sulphonation mixture described below are added in the course of 10 minutes. During this addition, the temperature rises to 95° C. After a short time, the 1-naphthylamine-4,6-disulphonic acid starts to crystallise out. The mixture is allowed to cool slowly to 60° C., whilst stirring slowly, and is kept at this temperature for one hour, and the hot 60° C. suspension is filtered. The filter cake is washed with a little 40% strength sulphuric acid and sucked thoroughly dry.

217 g of 1-naphthylamine-4,6-disulphonic acid are obtained in the form of slightly pink-coloured crystals moistened with sulphuric acid.

The composition of the crystals was determined by high pressure liquid chromatography and thin layer chromatography. The composition is: 65.0% by weight of 1-naphthylamine-4,6-disulphonic acid; 0.5% by weight of 1-naphthylamine-3,6-disulphonic acid; 0.5% by weight of 1-naphthylamine-2,4,6-trisulphonic acid; and 34.0% by weight of water/sulphuric acid.

The sulphonation mixture used had been obtained as follows:

780 g of oleum (25% strength) were initially introduced into a 1 l stirred apparatus. 225 g of 1-naphthylamine-6-sulphonic acid (about 99% pure) were introduced into this oleum at 20° C. in the course of about 30 minutes. The sulphonation mixture was then stirred at 50° C. for 4 hours.

What we claim is:

1. A process for the isolation of 1-napthylamine-4,6- or 1-naphthylamine-4,7-disulphonic acid from sulphonation mixtures obtained in the sulphonation of 1-napthylamine-6- or 1-naphthylamine-7-sulphonic acid, respectively with sulphuric acid and sulphur trioxide, wherein the aqueous solutions or suspensions formed when the sulphonation mixtures are introduced into water are warmed to 85° to 120° C. and the resulting solutions or suspensions are optionally kept for a period of time at this temperature, are then cooled to a temperature below 70° C., and the 1-naphthylamine-4,6- or 1-naphthylamine-4,7-disulphonic acid which has crystallised out is filtered off.

2. The process according to claim 1, wherein the aqueous solutions or suspensions formed when the sulphonation mixtures are introduced into water are warmed to 90° to 115° C.

3. The process according to claim 1, wherein the sulphuric acid concentration in the dilute aqueous solutions or suspensions of the sulphonation mixtures is 10 to 70% by weight.

4. The process according to claim 1, wherein the sulphuric acid concentration in the dilute aqueous solutions or suspensions of the sulphonation mixtures is 25 to 60% by weight.

* * * * *